(12) United States Patent
Kawase et al.

(10) Patent No.: US 9,010,404 B2
(45) Date of Patent: Apr. 21, 2015

(54) INSPECTION APPARATUS AND INSPECTION METHOD FOR HEAT TRANSFER TUBE

(75) Inventors: Naoto Kawase, Tokyo (JP); Hidetoshi Yonemura, Tokyo (JP); Toshihiro Kawashima, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 558 days.

(21) Appl. No.: 13/359,334

(22) Filed: Jan. 26, 2012

(65) Prior Publication Data

US 2012/0193065 A1 Aug. 2, 2012

(30) Foreign Application Priority Data

Feb. 2, 2011 (JP) ................................. 2011-021052

(51) Int. Cl.
*B60H 1/00* (2006.01)
*G01N 27/90* (2006.01)
*F22B 37/00* (2006.01)

(52) U.S. Cl.
CPC ............ *G01N 27/902* (2013.01); *F22B 37/005* (2013.01)

(58) Field of Classification Search
USPC ....................... 165/11.1, 76, 11.2; 29/890.031
See application file for complete search history.

(56) References Cited

U.S. PATENT DOCUMENTS

| | | | | |
|---|---|---|---|---|
| 4,337,431 A | * | 6/1982 | Hale | 324/220 |
| 4,438,805 A | * | 3/1984 | Gugel | 165/11.2 |
| 4,649,989 A | * | 3/1987 | Vermaat et al. | 165/11.2 |
| 4,804,291 A | * | 2/1989 | Everett | 403/287 |
| 4,984,627 A | * | 1/1991 | LeBourgeois | 165/11.2 |
| 5,025,854 A | * | 6/1991 | Richter et al. | 165/112 |
| 5,105,876 A | * | 4/1992 | Burack et al. | 165/11.2 |
| 5,247,251 A | * | 9/1993 | Yost et al. | 324/220 |

(Continued)

FOREIGN PATENT DOCUMENTS

| | | |
|---|---|---|
| DE | 44 12 042 A | 10/1995 |
| EP | 0 471 556 A1 | 2/1992 |
| GB | 1101011 A * | 1/1968 |

(Continued)

OTHER PUBLICATIONS

Extended European Search Report dated May 25, 2012, issued in corresponding European Patent Application No. 12152762.6 (7 pages).

(Continued)

*Primary Examiner* — Mohammad M Ali
*Assistant Examiner* — Raheena Rehman
(74) *Attorney, Agent, or Firm* — Westerman, Hattori, Daniels & Adrian, LLP (57) ABSTRACT

An inspection apparatus for a heat transfer tube is provided in an inspection robot to be fixed to a tube plate surface of a tube plate at which the heat transfer tube is opened and is for inspecting a seal-welded portion at which the heat transfer tube is welded to the tube plate. The inspection apparatus includes: an inserting unit to be inserted into and withdrawn from the heat transfer tube; a detecting unit having detecting unit for detecting the presence or absence of a defect at the seal-welded portion; a rotating mechanism for rotating the detecting unit around a central axis of the inserting unit; and a moving mechanism for moving, with respect to the inspection robot, the inserting unit, the detecting unit, and the rotating mechanism along the central axis for the rotation of the detecting unit.

7 Claims, 7 Drawing Sheets

(56) References Cited

U.S. PATENT DOCUMENTS

| | | |
|---|---|---|
| 5,611,948 A | 3/1997 | Hawkins |
| 7,234,347 B2 * | 6/2007 | Harthorn et al. ........... 73/152.57 |

FOREIGN PATENT DOCUMENTS

| | | |
|---|---|---|
| JP | 61-194352 A | 8/1986 |
| JP | 63-70077 U | 5/1988 |
| JP | 63-228057 A | 9/1988 |
| JP | 03-033651 A | 2/1991 |
| JP | 5322855 A | 12/1993 |
| JP | 6-148143 A | 5/1994 |
| JP | 10227765 A * | 8/1998 |
| JP | 11-174032 A | 7/1999 |
| JP | 3137576 B2 | 2/2001 |
| JP | 2005-262218 A | 9/2005 |
| JP | 2008-89328 A | 4/2008 |
| WO | 2011/074294 A1 | 6/2011 |

OTHER PUBLICATIONS

Japanese Office Action dated Aug. 19, 2014, issued in corresponding JP application No. 2011-021052 with English translation (8 pages).
Japanese Decision to Grant a Patent dated Oct. 28, 2014, issued in corresponding JP Patent Application No. 2011-021052 with English translation (4 pages).

* cited by examiner

INSPECTION APPARATUS AND INSPECTION METHOD FOR HEAT TRANSFER TUBE

FIELD

The present invention relates to a heat transfer tube inspection apparatus and inspection method, which are applied when inspecting a heat transfer tube of a heat exchanger.

BACKGROUND

For example, in a steam generator as a heat exchanger used in a pressurized water reactor (PWR), both ends of a number of inverted U-shaped heat transfer tubes are inserted through and fixed to tube plates inside a core barrel section thereof. This heat transfer tube is inspected for its soundness. Such an inspection includes an inspection for a seal-welded portion at a portion where the heat transfer tube is opened to the tube plate.

A defect (a flaw or the like) at the seal-welded portion may possibly be a cause for the formation of a path (leak path) from a primary cooling water side to a secondary cooling water side. Thus, an inspection for the seal-welded portion is performed when manufacturing the steam generator. Moreover, also during a periodic inspection performed after the service of the steam generator, there is a possibility for inspecting the seal-welded portion.

An eddy current testing (ECT) may be employed for this inspection since it can inspect a defect present on a surface of the seal-welded portion relatively at a high speed. Various methods have been suggested conventionally (for example, see Patent Literatures 1 and 2).

Moreover, there exist a large number of heat transfer tubes in the steam generator. Therefore, it takes a large amount of time for a worker to manually perform an inspection for such heat transfer tubes, and it is also a troublesome work. Thus, an increase in inspection speed and automation by a remote control are desired. Furthermore, during a periodic inspection performed after the service of the steam generator, since the inside of a water chamber to which the heat transfer tubes are opened is in a radiation atmosphere by being directly in contact with primary cooling water heated in the reactor, it is not preferable for a worker performing the inspection to stay in the water chamber for a long period of time. Thus, it is preferred to perform the inspection by a remote control from the outside of the water chamber. Conventionally, there has been suggested an inspection robot configured to be supported by a tube plate surface via a clamp mechanism inserted through a heat transfer tube and to be movable along the tube plate surface (for example, see Patent Literatures 3 and 4).

CITATION LIST

Patent Literature

Patent Literature 1: Japanese Patent Application Laid-Open No. Hei. 5-322855
Patent Literature 2: Japanese Patent Application Laid-Open No. 2005-262218
Patent Literature 3: Japanese Patent No. 3137576
Patent Literature 4: Japanese Patent Application Laid-Open No. Hei. 10-227765

SUMMARY

Technical Problem

When inspecting the seal-welded portion, a detecting unit is rotationally moved along a portion of the heat transfer tube opened to the tube plate. In order to rotationally move the detecting unit, a support unit for supporting the rotation is inserted into the heat transfer tube. However, since inspection is performed by a remote control from the outside of the water chamber, if the detecting unit is mounted in the above-described inspection robot, for example, it is required for the support unit to be pulled out from the heat transfer tube so that the support unit does not interfere with the movement of the inspection robot.

The present invention is to solve the above-described problem, and an object thereof is to provide a heat transfer tube inspection apparatus and inspection method capable of inspecting a seal-welded portion of a heat transfer tube by a remote control.

Solution to Problem

According to an aspect of the present invention, a heat transfer tube inspection apparatus provided in a fixed unit to be fixed to a tube plate surface of a tube plate at which a heat transfer tube is opened, for inspecting a seal-welded portion at which the heat transfer tube is welded to the tube plate, includes: an inserting unit to be inserted into and withdrawn from the heat transfer tube; a detecting unit having a detecting unit for detecting a presence or absence of a defect at the seal-welded portion; a rotating mechanism for rotating the detecting unit around a central axis of the inserting unit; and a moving mechanism for moving, with respect to the fixed unit, the inserting unit, the detecting unit, and the rotating mechanism along the central axis for the rotation of the detecting unit.

According to this heat transfer tube inspection apparatus, the moving mechanism moves the inserting unit, the detecting unit, and the rotating mechanism along the central axis for the rotation of the detecting unit. As a result, while it becomes possible to insert the inserting unit into the heat transfer tube to be inspected and to detect the presence or absence of a defect in the seal-welded portion of the heat transfer tube by the detecting unit, it becomes possible to withdraw the inserting unit from the heat transfer tube and to move the fixed unit to a position of another heat transfer tube to be inspected. As a result, it is possible to inspect the seal-welded portion of the heat transfer tube by a remote control.

Advantageously, the heat transfer tube inspection apparatus further includes a slide movement mechanism for sliding, with respect to the fixed unit, at least the inserting unit, the detecting unit, and the rotating mechanism in a direction perpendicular to the central axis for the rotation of the detecting unit.

According to this heat transfer tube inspection apparatus, even if the position of the central axis for the rotation of the detecting unit is misaligned with respect to the heat transfer tube to be inspected, the inserting unit, the detecting unit, and the rotating mechanism are slid by means of the slide movement mechanism in a direction perpendicular to the central axis for the rotation of the detecting unit, thereby absorbing such misalignment. Then, while the inserting unit is inserted into the heat transfer tube to be inspected, the detecting unit is rotated along the seal-welded portion of the heat transfer tube. Therefore, it is possible to improve the inspection accuracy thereof.

Advantageously, the heat transfer tube inspection apparatus further includes a rotation angle detecting unit for detecting a rotation angle of the detecting unit.

According to this heat transfer tube inspection apparatus, the rotational position of the detecting unit can be aligned so as to correspond to the direction in which the heat transfer tube is attached to the tube plate. As a result, it facilitates to identify the position at which a defect of the seal-welded portion is detected, thereby improving the inspection accuracy.

Advantageously, the heat transfer tube inspection apparatus further includes a fixing mechanism provided in the inserting unit, for fixing the inserting unit inside the heat transfer tube.

According to this heat transfer tube inspection apparatus, when the detecting unit is rotated, positional misalignment in the central axis for the rotation thereof is prevented from occurring, thereby rotating the detecting unit along the seal-welded portion of the heat transfer tube. Thus, it is possible to improve the inspection accuracy.

Advantageously, in the heat transfer tube inspection apparatus, a plurality of sets of at least the inserting unit, the detecting unit, and the rotating mechanism are provided with a distance between the central axes thereof being based on an arrangement distance between the heat transfer tubes.

According to this heat transfer tube inspection apparatus, a plurality of heat transfer tubes to be inspected can be simultaneously inspected, thereby making it possible to shorten the inspection time.

Advantageously, in the heat transfer tube inspection apparatus, the moving mechanism is provided for each of the sets.

For example, in the steam generator, in a case where a stay rod provided between the respective tube support plates for supporting the heat transfer tubes is placed between the heat transfer tubes, or in a case where the heat transfer tube is disposed at a peripheral portion of the tube plate, there is a case where all of the sets cannot be used. Therefore, according to this heat transfer tube inspection apparatus, the inserting unit, the detecting unit, and the rotating mechanism disposed at a portion with no heat transfer tube are not moved, whereas the inserting unit, the detecting unit, and the rotating mechanism disposed at a portion with the heat transfer tube are moved by the moving mechanism. Thus, it is possible to perform inspection without blind spots.

According to another aspect of the present invention, a heat transfer tube inspection method for inspecting a seal-welded portion at which a heat transfer tube is welded to a tube plate by using an inspection apparatus provided in fixed unit to be fixed to a tube plate surface of the tube plate at which the heat transfer tube is opened and includes: an inserting unit to be inserted into and withdrawn from the heat transfer tube; a detecting unit having detecting unit for detecting a presence or absence of a defect at the seal-welded portion; a rotating mechanism for rotating the detecting unit around a central axis of the inserting unit; a moving mechanism for moving, with respect to the fixed unit, the inserting unit, the detecting unit, and the rotating mechanism along the central axis for the rotation of the detecting unit; and rotation angle detecting unit for detecting a rotation angle of the detecting unit. The inspection method includes: detecting a rotation angle of the detecting unit by the rotation angle detecting unit with the fixed unit being fixed to the tube plate surface of the tube plate; next, moving the inserting unit by the moving mechanism to insert the inserting unit into the heat transfer tube and to cause the detecting unit of the detecting unit to face to the seal-welded portion; and next, rotating the detecting unit by the rotating mechanism based on the detected rotation angle.

According to this heat transfer tube inspection method, the moving mechanism moves the inserting unit, the detecting unit, and the rotating mechanism along the central axis for the rotation of the detecting unit. As a result, while it becomes possible to insert the inserting unit into the heat transfer tube to be inspected and to detect the presence or absence of a defect in the seal-welded portion of the heat transfer tube by the detecting unit, it becomes possible to withdraw the inserting unit from the heat transfer tube and to move the fixed unit to a position of another heat transfer tube to be inspected. As a result, it is possible to inspect the seal-welded portion of the heat transfer tube by a remote control. Furthermore, with the step of detecting a rotation angle of the detecting unit by the rotation angle detecting unit, the rotational position of the detecting unit can be aligned so as to correspond to the direction in which the heat transfer tube is attached to the tube plate. As a result, it facilitates to identify the position at which a defect of the seal-welded portion is detected, thereby improving the inspection accuracy.

Advantageously, in the heat transfer tube inspection method, the detecting unit is rotated in forward and reverse directions around the central axis in the rotating the detecting unit by the rotating mechanism.

According to this heat transfer tube inspection method, the detecting unit is rotated in forward and reverse directions around the central axis, and accordingly, it is possible to make a determination based on the combination of the inspection signals in both of the forward and reverse rotations. Therefore, more accurate inspection can be performed.

Advantageous Effects of Invention

According to the present invention, it is possible to inspect a seal-welded portion in a heat transfer tube by a remote control.

DESCRIPTION OF EMBODIMENTS

An embodiment according to the present invention will be described below in detail with reference to the drawings. Note that the present invention is not limited by this embodiment. Moreover, constituent elements in the following embodiment include those which can be substituted and easily made by those skilled in the art or those substantially the same.

Figure 1:
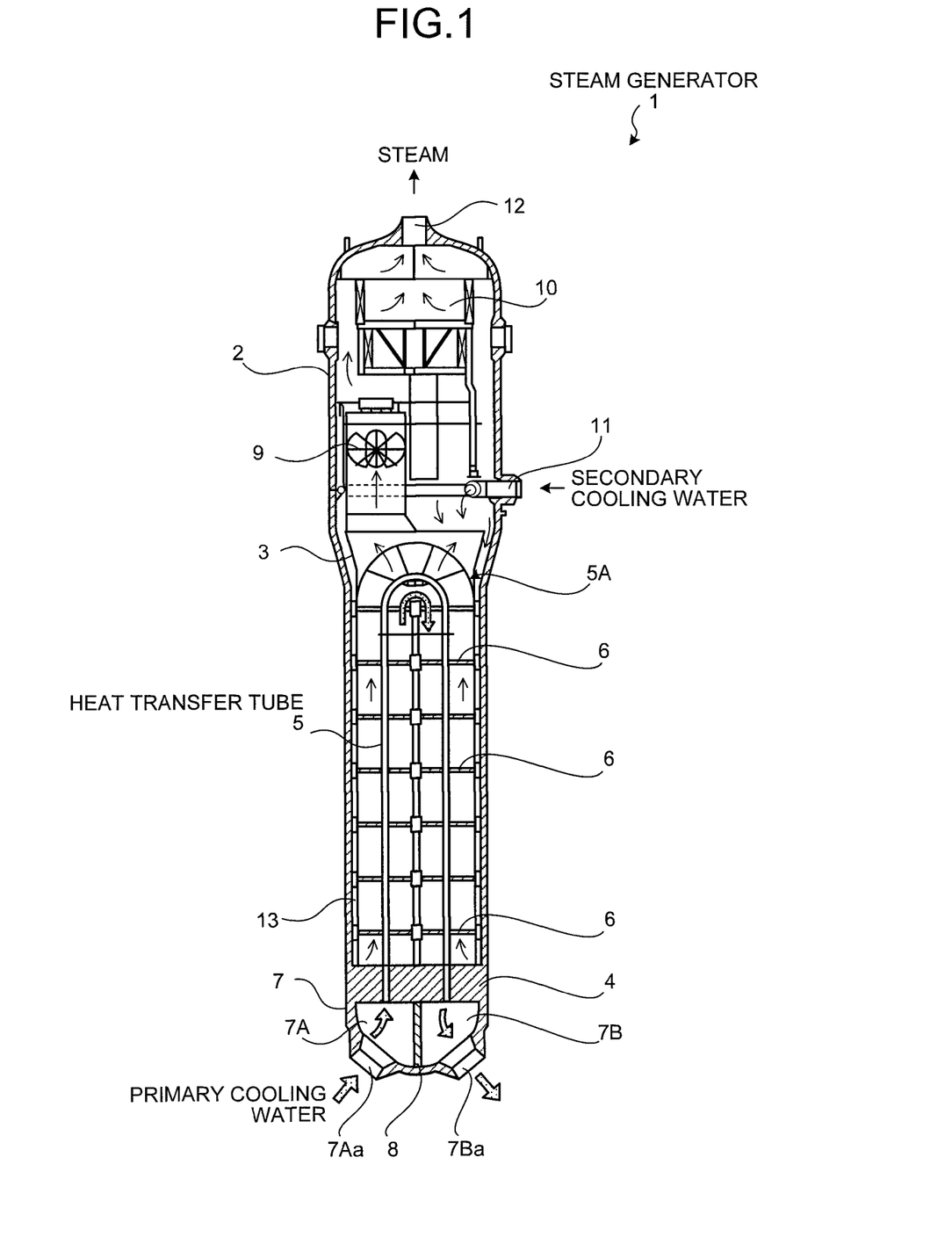
FIG. 1 is a schematic cross-sectional side view of a steam generator.

FIG. 1 is a schematic cross-sectional side view of a steam generator. A steam generator 1 as a heat exchanger is used in a pressurized water reactor (PWR), for example. The pressurized water reactor uses light water as a reactor coolant and a neutron moderator. The pressurized water reactor sends, to the steam generator 1, primary cooling water as high-temperature and high-pressure water so that the light water does not boil throughout the reactor. In the steam generator 1, heat of the high-temperature and high-pressure primary cooling water is transferred to secondary cooling water, thereby generating steam from the secondary cooling water. Then, this steam turns a turbine generator to generate electricity.

The steam generator 1 has a core barrel section 2 that is vertically elongated and forms a sealed hollow cylindrical shape. The lower half thereof has a slightly smaller diameter than the upper half thereof. The core barrel section 2 includes a cylindrical tube bundle shroud 3, which is disposed in a lower half thereof with a predetermined distance from an inner wall surface of the core barrel section 2. The lower end portion of the cylindrical tube bundle shroud 3 extends to the vicinity of a tube plate 4 that is disposed on a lower side of the lower half of the core barrel section 2. Inside the cylindrical tube bundle shroud 3, a heat transfer tube bundle 5A is provided. The heat transfer tube bundle 5A is formed by a plurality of inverted U-shaped heat transfer tubes 5. Each heat transfer tube 5 is disposed with a U-shaped circular arc portion thereof pointing upward. Lower end portions of the heat transfer tubes 5 are inserted through and supported by tube holes of the tube plate 4, and middle portions thereof are supported by the cylindrical tube bundle shroud 3 via a plurality of tube support plates 6. The tube support plate 6 is provided with a plurality of heat transfer tube insertion holes, and the heat transfer tubes 5 are inserted through the heat transfer tube insertion holes so that the tube support plate 6 supports the heat transfer tubes 5.

The core barrel section 2 includes a water chamber 7 at a lower end portion thereof. The interior of the water chamber 7 is divided into an inlet chamber 7A and an outlet chamber 7B by a partition wall 8. One end of the heat transfer tube 5 is communicated with the inlet chamber 7A, and the other end of the heat transfer tube 5 is communicated with the outlet chamber 7B. The inlet chamber 7A is provided with an inlet nozzle 7Aa to be communicated with outside of the core barrel section 2. The outlet chamber 7B is provided with an outlet nozzle 7Ba to be communicated with outside of the core barrel section 2. A cooling water tube (not shown in the drawings) through which primary cooling water is sent from the pressurized water reactor is connected to the inlet nozzle 7Aa. A cooling water tube (not shown in the drawing) through which primary cooling water that has been subjected to heat exchange is sent to the pressurized water reactor is connected to the outlet nozzle 7Ba.

Inside the upper half of the core barrel section 2, there are provided a steam-water separator 9 for separating feed water into steam and hot water, and a moisture separator 10 for reducing moisture of the separated steam to obtain a state close to dry steam. A feed water tube 11 for feeding secondary cooling water from outside to the inside of the core barrel section 2 is inserted between the steam-water separator 9 and the heat transfer tube bundle 5A. Furthermore, the core barrel section 2 includes a steam outlet 12 formed at the upper end thereof. Moreover, the core barrel section 2 includes, within the lower half thereof, a feed water line 13 for having secondary cooling water fed from the feed water tube 11 to the inside of the core barrel section 2 flow down between the core barrel section 2 and the tube bundle shroud 3, turn up at the tube plate 4, and rise along the heat transfer tube bundle 5A. Note that a cooling water tube (not shown in the drawing) for sending steam to a turbine is connected to the steam outlet 12, and a cooling water tube (not shown in the drawing) for feeding secondary cooling water obtained by cooling the steam used in the turbine in a condenser (not shown in the drawing) is connected to the feed water tube 11.

In such a steam generator 1, the primary cooling water heated in the pressurized water reactor is sent to the inlet chamber 7A and circulated through a number of heat transfer tubes 5 to reach the outlet chamber 7B. On the other hand, the secondary cooling water cooled by the condenser is sent to the feed water tube 11, passes through the feed water line 13 inside the core barrel section 2, and rises up along the heat transfer tube bundle 5A. Here, heat exchange between the high-pressure and high-temperature primary cooling water and the secondary cooling water is performed inside the core barrel section 2. Then, the cooled primary cooling water is returned to the pressurized water reactor from the outlet chamber 7B. On the other hand, the secondary cooling water that has been heat-exchanged with the high-pressure and high-temperature primary cooling water rises inside the core barrel section 2 and is separated into steam and hot water by the steam-water separator 9. Then, the separated steam is subjected to moisture reduction at the moisture separator 10 and then sent to the turbine.

After the service of the steam generator 1, the heat transfer tubes 5 of such a steam generator 1 are inspected simultaneously with the time when the operation of the core is periodically stopped for a refueling operation, for example. In this inspection, since the inside of the water chamber 7 is in a radiation atmosphere by being directly in contact with the primary cooling water heated in the reactor, it is not preferable for a worker performing the inspection to stay inside the water chamber 7 for a long period of time. Thus, an inspection apparatus for performing the inspection by a remote control from the outside of the water chamber 7 is used.

Figure 2:
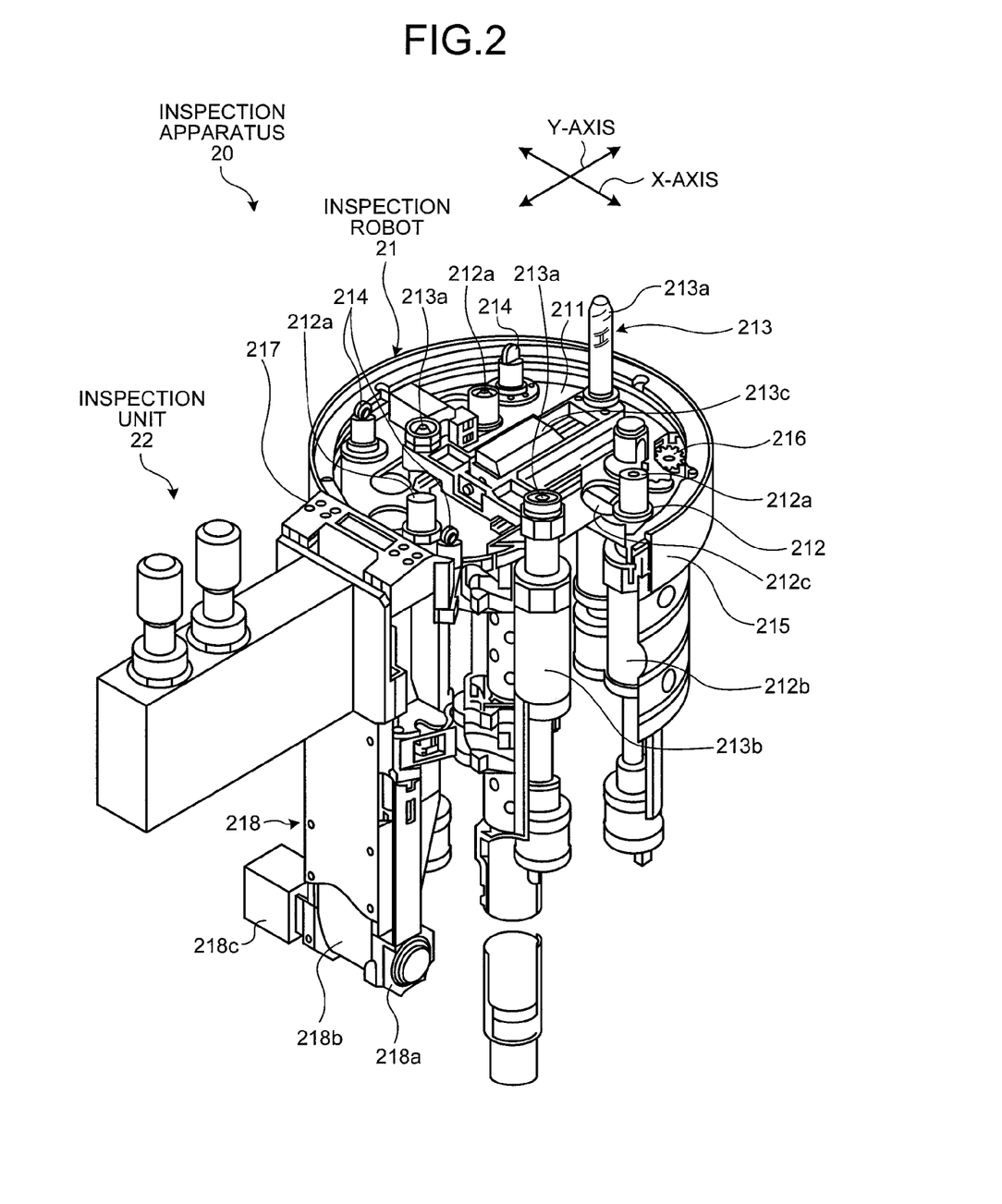
FIG. 2 is a perspective view showing a heat transfer tube inspection apparatus according to an embodiment of the present invention.
Figure 3:
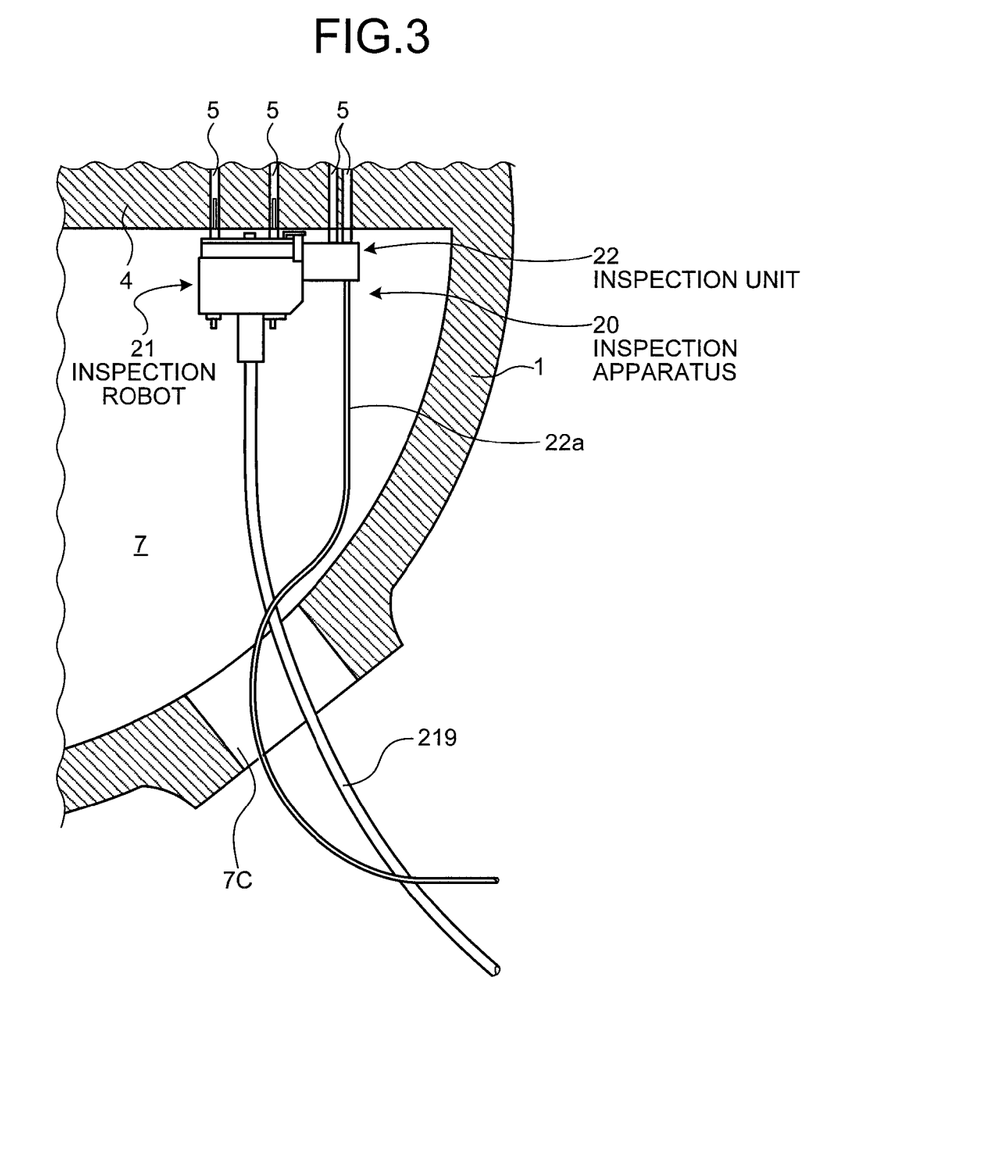
FIG. 3 is a schematic diagram showing a state in which the heat transfer tube inspection apparatus according to the embodiment of the present invention is used.

FIG. 2 is a perspective view showing a heat transfer tube inspection apparatus according to the present embodiment, and FIG. 3 is a schematic diagram showing a state in which the heat transfer tube inspection apparatus according to the present embodiment is used. As shown in FIG. 2, an inspection apparatus 20 for the heat transfer tube 5 in the present embodiment includes, inside the water chamber 7, an inspection robot 21 which is fixed means to be fixed to a tube plate surface (a lower surface of the tube plate 4) at which the heat transfer tube 5 is opened. Note that the fixed means may be another means fixed to the tube plate surface (the lower surface of the tube plate 4) at which the heat transfer tube 5 is opened, for example, a manipulator disposed inside the water chamber 7 although not explicitly shown in the drawing, and is not limited to the inspection robot 21.

As shown in FIG. 2, the inspection robot 21 includes an X-axis direction walking device 212 and a Y-axis direction walking device 213 provided on a circular substrate 211 (represented by an X-axis and a Y-axis orthogonal to each other two-dimensionally along the tube plate surface). The X-axis direction walking device 212 includes three clamp shafts 212a. The clamp shafts 212a are inserted into the heat transfer tubes 5 opened at the tube plate surface via clamp cylinders 212b, respectively and expanded to be fixed within the heat transfer tubes 5, whereas they are pulled out from the heat transfer tubes 5 while releasing the expansion by the clamp cylinders 212b. Moreover, the X-axis direction walking device 212 includes an X-axis driving cylinder 212c. The X-axis driving cylinder 212c moves two clamp shafts 212a in the X-axis direction by one pitch of the heat transfer tube 5.

Similarly, the Y-axis direction walking device 213 includes three clamp shafts 213a. The clamp shafts 213a are inserted into the heat transfer tubes 5 opened at the tube plate surface via clamp cylinders 213b, respectively and expanded to be fixed within the heat transfer tubes 5, whereas they are pulled out from the heat transfer tubes 5 while releasing the expansion by the clamp cylinders 213b. Moreover, the Y-axis direction walking device 213 includes a Y-axis driving cylinder 213c. The Y-axis driving cylinder 213c moves two clamp shafts 213a in the Y-axis direction by one pitch of the heat transfer tube 5.

Moreover, the inspection robot 21 includes a plurality of (three in the present embodiment) guide rollers 214 provided on the substrate 211.

Moreover, the inspection robot 21 includes a rotation base 215 provided at a periphery of the substrate 211. The rotation base 215 is driven by a predetermined angle in a circumferential direction of the substrate 211 by a drive unit 216. The rotation base 215 is provided with an attachment plate 217. A lifting mechanism 218 is attached to this attachment plate 217. In the lifting mechanism 218, a lifting base 218a is connected to the attachment plate 217 via a belt 218b. The belt 218b lifts the lifting base 218a up and down by a drive motor 218c. An inspection unit 22 to be described later is attached to this lifting base 218a.

Such an inspection robot 21 makes a walking movement in two-dimensional directions along the tube plate surface by the X-axis direction walking device 212 and the Y-axis direction walking device 213 with a length of stride thereof being one pitch of the heat transfer tubes 5 disposed in the tube plate 4 at predetermined pitches. During this walking movement, the guide rollers 214 guide the movement while being in contact with the tube plate surface. Since the inspection robot 21 is thereby moved to a desired position on the tube plate surface and fixed thereon as shown in FIG. 3, it becomes possible to perform a predetermined inspection by disposing the inspection unit 22 at a position of the heat transfer tube 5 to be inspected. Moreover, since the inspection unit 22 makes a rotational movement by rotating the rotation base 215 as necessary, it becomes possible for the inspection robot 21 to perform a predetermined inspection by disposing the inspection unit 22 at a position of the heat transfer tube 5 to be inspected.

Note that a detachable long control rod (not shown in the drawing) is attached to the inspection robot 21 prior to the inspection of the heat transfer tube 5. A worker holds and inserts this control rod into the water chamber 7 through a manhole 7C so as to position the inspection robot 21 on the tube plate surface of the tube plate 4 directly above the manhole 7C. Then, the inspection robot 21 inserts the respective clamp shafts 212a and 213a of the X-axis direction walking device 212 and the Y-axis direction walking device 213 into the heat transfer tubes 5 to perform clamping. Thereafter, by removing the control rod, the inspection robot 21 is installed on the tube plate surface of the tube plate 4 with an operating cable 219 extending from the substrate 211 being withdrawn from the manhole 7C to the outside of the water chamber 7. After installing the inspection robot 21 to the tube plate 4 as described above, the drive motor 218c of the lifting mechanism 218 is operated to extend the belt 218b downwardly from a position shown in FIG. 2, thereby lowering the lifting base 218a down to the manhole 7C. Then, the inspection unit 22 is attached to this lifting base 218a, and the drive motor 218c is operated again to accommodate the belt 218b upward and restore the lifting base 218a to the original position shown in FIG. 2. A cable 22a connected to the inspection unit 22 takes a form withdrawn from the manhole 7C to the outside of the water chamber 7, thereby completing a preparation for inspection.

Figure 4:
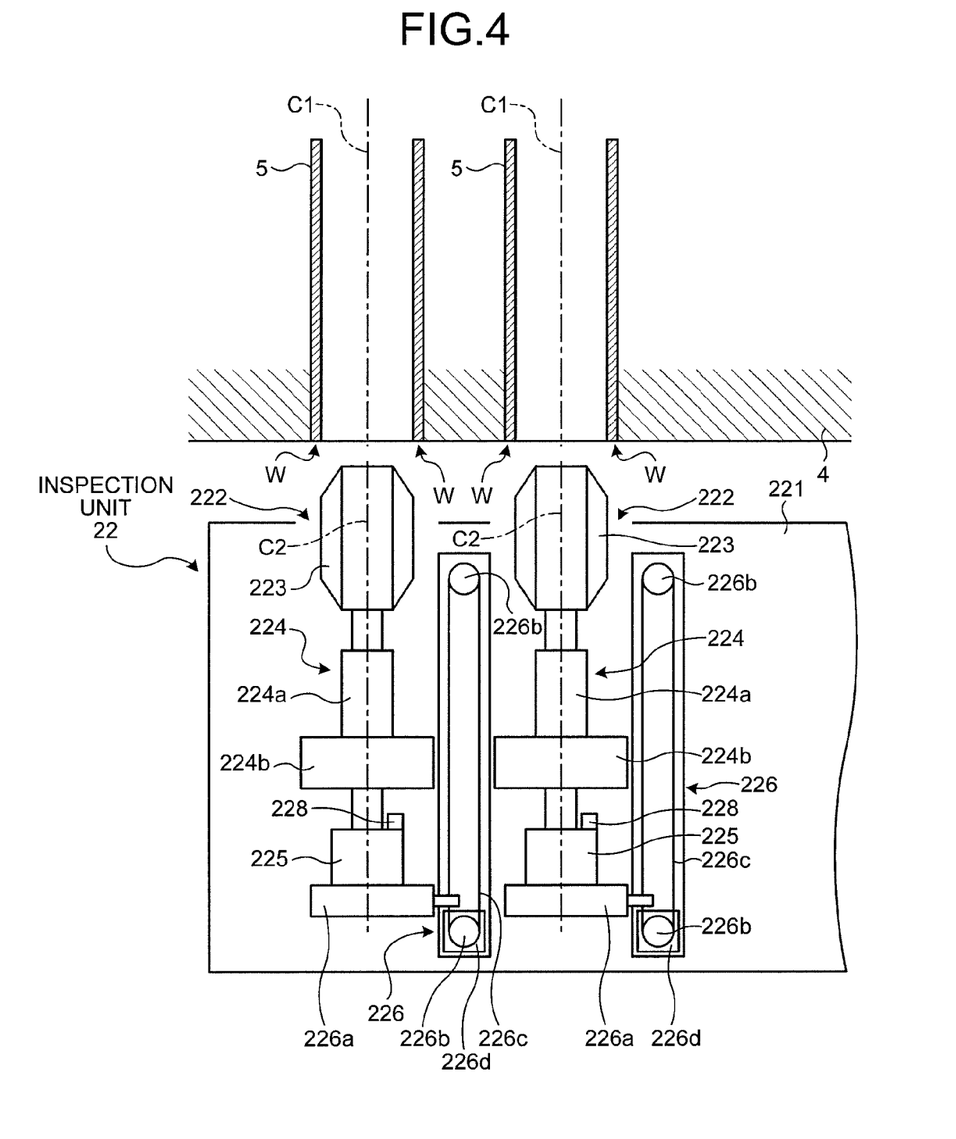
FIG. 4 is a cross-sectional side view showing an inspection unit of the heat transfer tube inspection apparatus according to the embodiment of the present invention.
Figure 5:
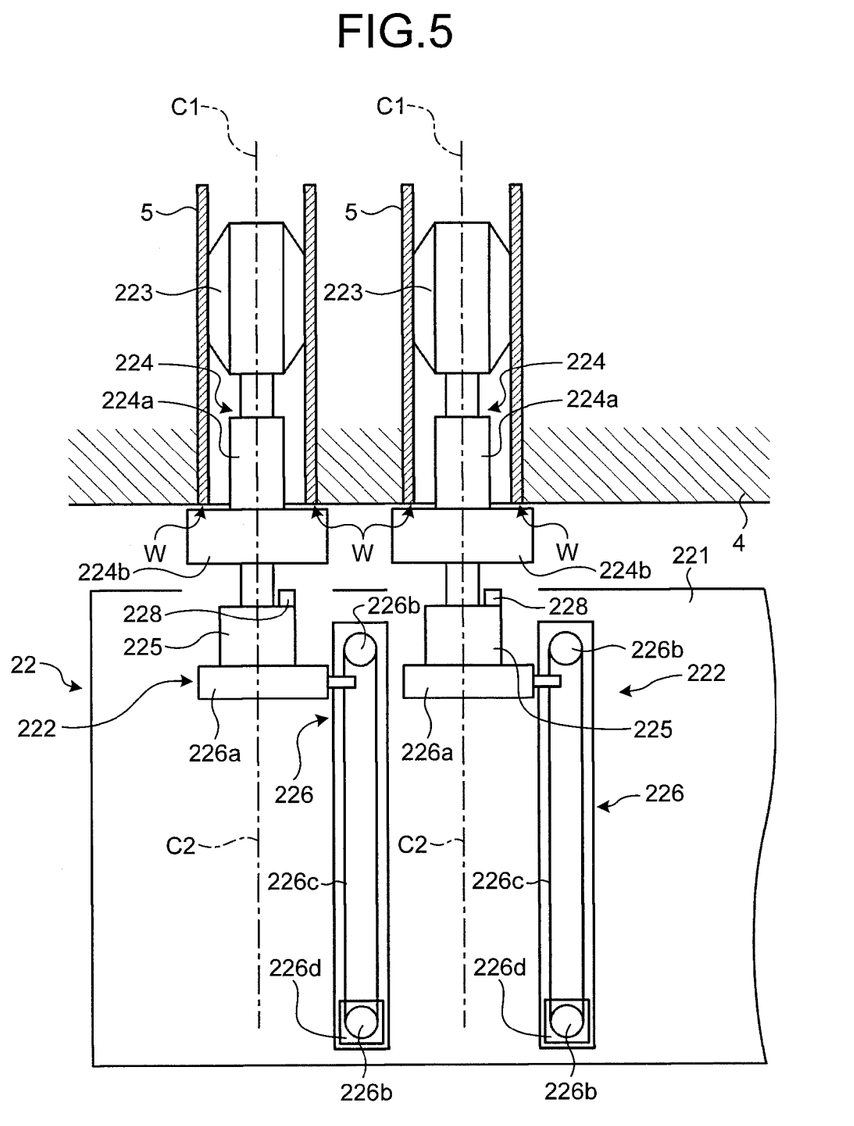
FIG. 5 is a cross-sectional side view showing an operation of the inspection unit of the heat transfer tube inspection apparatus according to the embodiment of the present invention.
Figure 6:
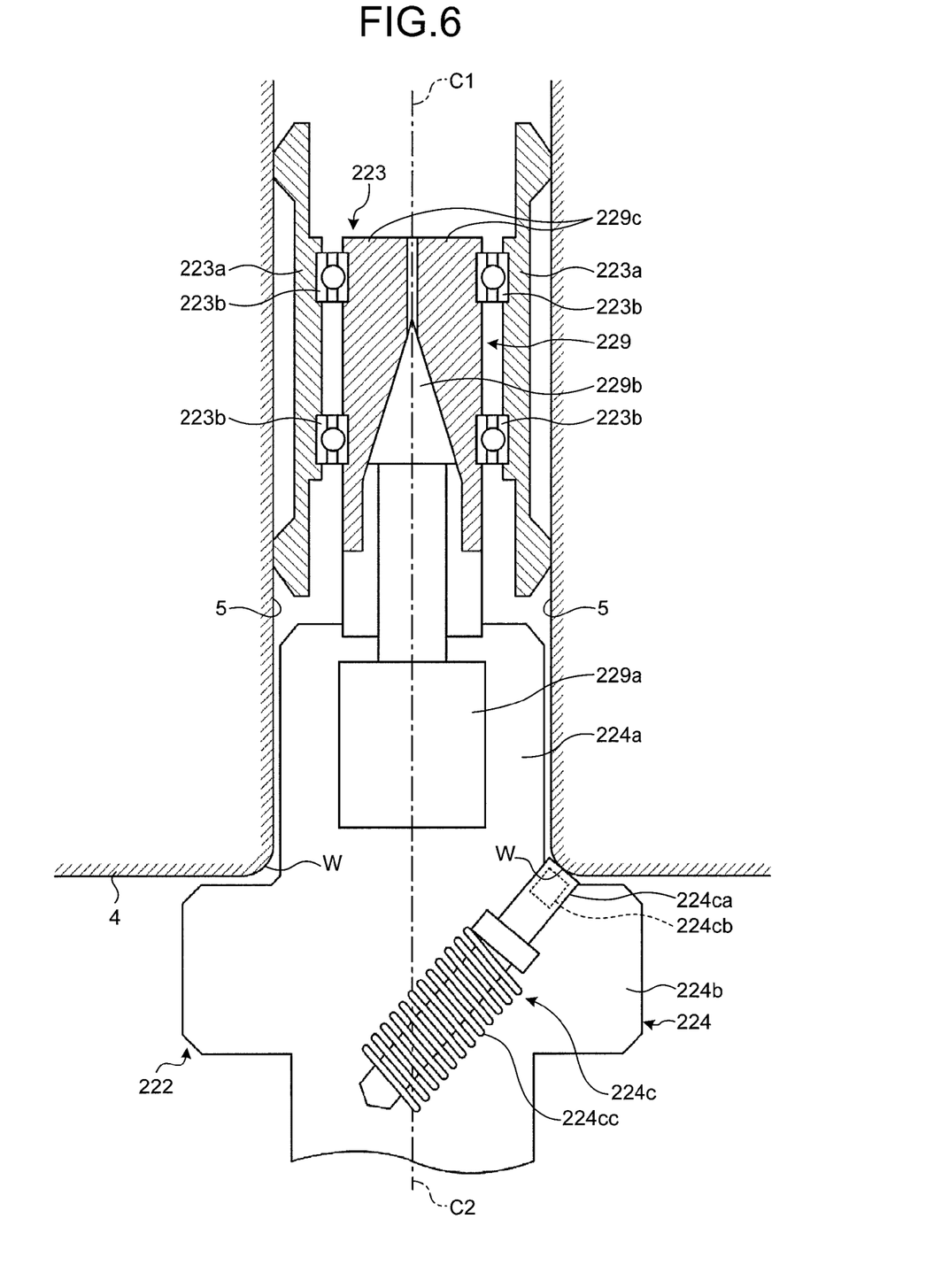
FIG. 6 is an enlarged cross-sectional view showing an inserting unit and a detecting unit of the inspection unit.
Figure 7:
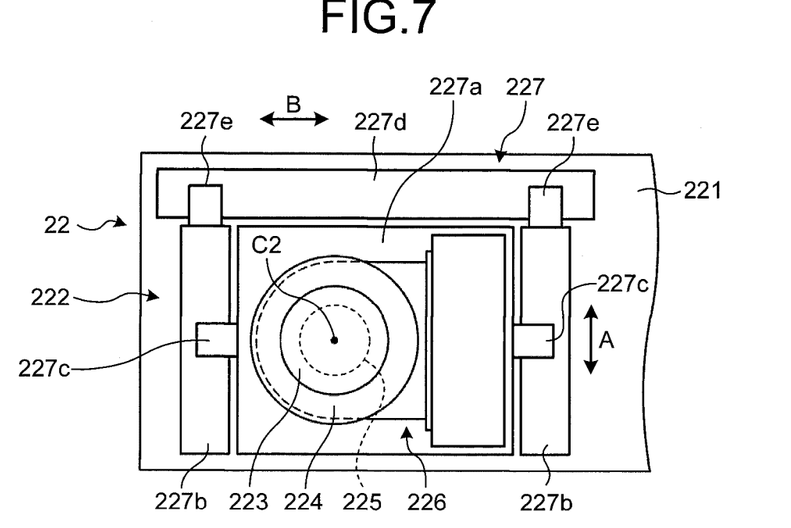
FIG. 7 is a partial enlarged plan view of the inspection unit.

FIG. 4 is a cross-sectional side view showing the inspection unit of the heat transfer tube inspection apparatus according to the present embodiment. FIG. 5 is a cross-sectional side view showing an operation of the inspection unit. FIG. 6 is an enlarged cross-sectional view showing an inserting unit and a detecting unit of the inspection unit. FIG. 7 is a partial enlarged plan view of the inspection unit. Note that FIGS. 4 and 5 show a state in which the inspection unit 22 is attached to the inspection robot 21 as the fixed means as described above and the inspection robot 21 is fixed to the tube plate surface of the tube plate 4.

As shown in FIGS. 4 and 5, the inspection unit 22 includes inspecting probe units 222 for inspecting seal-welded portions W, which are provided for the inspection robot 21 as fixed means, specifically an attachment base 221 to be attached to the lifting base 218a of the lifting mechanism 218.

The inspecting probe unit 222 includes an inserting unit 223, a detecting unit 224, a rotating mechanism 225, and a moving mechanism 226.

As shown in FIGS. 4 and 5, the inserting unit 223 is to be inserted into and withdrawn from the heat transfer tube 5. The inserting unit 223 is configured so that when the inserting unit 223 is inserted into the heat transfer tube 5, the periphery thereof is pressed against an inner peripheral surface of the heat transfer tube 5 so as to stay inside the heat transfer tube 5. For example, as shown in FIG. 6, the inserting unit 223 is configured to include an elastically deformable contact member 223a at the periphery thereof and to be pressed against the inner peripheral surface of the heat transfer tube 5 by the elastic deformation of the contact member 223a. A central axis C2 of the inserting unit 223 inserted into the heat transfer tube 5 coincides with a central axis C1 of the heat transfer tube 5. Moreover, a tip portion of the inserting unit 223 facing the heat transfer tube 5 has a tapered surface tapered off toward the heat transfer tube 5. This facilitates the insertion into the heat transfer tube 5 and makes it possible to insert the inserting unit 223 into the heat transfer tube 5, even if the position of the central axis C2 of the inserting unit 223 is misaligned with the central axis C1 of the heat transfer tube 5, by absorbing such misalignment.

The detecting unit 224 is connected to the inserting unit 223 with a central axis thereof being the same as the central axis C2 of the inserting unit 223. The detecting unit 224 includes a columnar portion 224a whose tip is connected to the inserting unit 223, and a flange portion 224b formed in a projecting manner around a base end of the columnar portion 224a. The columnar portion 224a is formed to have a diameter to be inserted into the heat transfer tube 5 together with the inserting unit 223. The flange portion 224b is formed to have a diameter larger than the opening of the heat transfer tube 5. That is, as shown in FIG. 5, the detecting unit 224 is configured so that the flange portion 224b faces to the seal-welded portion W with the columnar portion 224a being inserted into the heat transfer tube 5. As shown in FIG. 6, the detecting unit 224 is provided with detecting means 224c for detecting the presence or absence of a defect in the seal-welded portion W at the portion of the flange portion 224b facing to the seal-welded portion W.

As shown in FIG. 6, the detecting means 224c is configured to include a contact 224ca, an ECT coil 224cb, and a pressing portion 224cc.

The contact 224ca includes the ECT coil 224cb provided therein. Along with the ECT coil 224cb, the contact 224ca is provided in the portion of the flange portion 224b facing to the seal-welded portion W so as to move closer to or away from the seal-welded portion W. By conducting a high-frequency current through the ECT coil 224cb, an eddy current is generated in a metal portion of an object to be inspected due to electromagnetic induction. If there is a defect (a flaw or the like) in the object to be inspected, the eddy current changes.

Thus, if a change in the eddy current is detected, it is thereby detected that the object to be inspected has a defect. The pressing portion 224cc is formed by an elastic body such as a compression coil spring. The pressing portion 224cc is accommodated in the flange portion 224b, and is for pressing and biasing the contact 224ca toward the outward of the flange portion 224b and in a direction approaching to the seal-welded portion W. That is, the contact 224ca is constantly pressed by the pressing portion 224cc so as to be in contact with the seal-welded portion W in a state where the flange portion 224b faces to the seal-welded portion W. As a result, the ECT coil 224cb is supported so as to constantly maintain the same distance from the seal-welded portion W. Note that although single detecting means 224c may be provided, a plurality of detecting means 224c may be provided at regular intervals from the central axis C2 and at regular intervals in the circumferential direction of the flange portion 224b. By providing a plurality of detecting means 224c, the presence or absence of a defect can be detected by each of the ECT coils 224cb thereof, thereby improving the detection accuracy.

As shown in FIGS. 4 and 5, the rotating mechanism 225 is for rotating the detecting unit 224 around the central axis C1 of the heat transfer tube 5 into which the inserting unit 223 is inserted. The rotating mechanism 225 is configured to include a motor connected to the base end of the detecting unit 224 and the side of the flange portion 224b. By driving the motor, the detecting unit 224 is rotated around the central axis C2. Note that since the detecting unit 224 is connected to the inserting unit 223 as described above, if the detecting unit 224 is rotated by the rotating mechanism 225, such a rotation is transmitted to the inserting unit 223. However, as shown in FIG. 6, the inserting unit 223 is provided with bearings 223b between the contact member 223a to be pressed against the inner peripheral surface of the heat transfer tube 5 and an inner portion thereof so that they are rotated relative to each other around the central axis C2. Therefore, there is no possibility of transmitting the rotation by the rotating mechanism 225 to the contact member 223a to be pressed against the inner peripheral surface of the heat transfer tube 5, and the inserting unit 223 is allowed to stay inside the heat transfer tube 5.

As shown in FIGS. 4 and 5, the moving mechanism 226 is for moving the inserting unit 223, the detecting unit 224, and the rotating mechanism 225 along the central axis C2 for the rotation of the detecting unit 224 with respect to the inspection robot 21 as fixed means, specifically the attachment base 221 to be attached to the lifting base 218a of the lifting mechanism 218. The moving mechanism 226 is configured to include a support base 226a for supporting the rotating mechanism 225, an endless belt 226c provided with respect to the attachment base 221 so as to be able to make a circular movement in a vertical direction between a pair of rollers 226b, and a motor 226d for having the belt 226c make a circular movement. That is, in the moving mechanism 226, the belt 226c makes a circular movement by driving the motor 226d. Accompanied by such a movement, the support base 226a moves up and down, thereby moving up and down the inserting unit 223, the detecting unit 224, and the rotating mechanism 225 along the central axis C2. The inserting unit 223 moved by this moving mechanism 226 takes a form withdrawn from the heat transfer tube 5 as shown in FIG. 4 or a form inserted into the heat transfer tube 5 as shown in FIG. 5. Moreover, the detecting unit 224 moved by the moving mechanism 226 takes a form in which the columnar portion 224a is withdrawn from the heat transfer tube 5 as shown in FIG. 4, or a form in which the columnar portion 224a is inserted into the heat transfer tube 5 so that the detecting means 224c at the flange portion 224b faces to the seal-welded portion W as shown in FIG. 5. The form in which the columnar portion 224a is withdrawn from the heat transfer tube 5 as shown in FIG. 4 and the form in which the detecting means 224c faces to the seal-welded portion W as shown in FIG. 5 can be recognized by detecting the number of steps obtained by the application of a stepping motor to the motor 226d, detecting a moved position by various sensors, or detecting a torque change in the motor 226d. Although not explicitly shown in the drawing, the moving mechanism 226 may be a mechanism employing an actuator (a hydraulic cylinder, a pneumatic cylinder, an electric motor, a hydraulic motor, or the like).

Moreover, as shown in FIG. 7, the inspecting probe unit 222 further includes a slide movement mechanism 227. The slide movement mechanism 227 is for sliding the inserting unit 223, the detecting unit 224, the rotating mechanism 225, and the moving mechanism 226 in a direction perpendicular to the central axis C2 for the rotation of the detecting unit 224 with respect to the inspection robot 21 as fixed means, specifically the attachment base 221 to be attached to the lifting base 218a of the lifting mechanism 218. The slide movement mechanism 227 forms a single unit including the inserting unit 223, the detecting unit 224, the rotating mechanism 225, the moving mechanism 226, and rotation angle detecting means 228 to be described later, and this unit is disposed on a slide table 227a. With respect to a pair of slide rails 227b that are perpendicular to the central axis C2 and extend in a horizontal direction (a direction of an arrow A in FIG. 7) with the inspection robot 21 as fixed means being fixed on the tube plate surface of the tube plate 4, the slide table 227a is provided so as to be movable in the extending direction of the slide rails 227b via respective sliders 227c. Moreover, with respect to a slide rail 227d, which is perpendicular to the central axis C2 and the slide rails 227b and extends in a horizontal direction (a direction of an arrow B in FIG. 7) to be fixed to the attachment base 221 with the inspection robot 21 as fixed means being fixed on the tube plate surface of the tube plate 4, the respective slide rails 227b are provided so as to be movable in the extending direction of the slide rail 227d via respective sliders 227e. Thus, the slide table 227a makes a slide movement by the slide rails 227b and the slide rail 227d with respect to the attachment base 221 in a horizontal direction with the inspection robot 21 as fixed means being fixed on the tube plate surface of the tube plate 4. As a result, the inserting unit 223, the detecting unit 224, the rotating mechanism 225, and the moving mechanism 226 disposed on the slide table 227a slide with respect to the attachment base 221 in a horizontal direction with the inspection robot 21 as fixed means being fixed on the tube plate surface of the tube plate 4. Note that each of the sliders 227c moving on the slide rails 227b is preferably supported by a spring or the like so as to stay at a reference position which is the center portion of the slide rail 227b in the extending direction thereof. Moreover, each of the sliders 227e moving on the slide rail 227d is preferably supported by a spring or the like so as to stay at a reference position which is the center portion of the slide rail 227d in the extending direction thereof.

Moreover, the inspecting probe unit 222 includes the rotation angle detecting means 228 for detecting a rotation angle of the detecting unit 224 as shown in FIGS. 4 and 5. The rotation angle detecting means 228 is to detect a rotation angle of the detecting means 224c of the detecting unit 224 rotated by the above-described rotating mechanism 225, i.e., to detect an absolute direction of the rotation of the detecting means 224c with respect to the surface of the earth or the like.

Examples of such absolute rotation angle detecting means 228 include a combination of a gyrosensor and an acceleration sensor, for example. This may be attached on the side of the rotating mechanism 225 as shown in FIGS. 4 and 5, or may be attached on the side of the detecting unit 224 although not explicitly shown in the drawings. With this configuration, a rotational position of the detecting means 224c is detected. Note that the rotation angle detecting means 228 may be anything other than the combination of a gyrosensor and an acceleration sensor as long as it can detect an absolute direction for the rotation of the detecting means 224c.

Moreover, as shown in FIG. 6, the inspecting probe unit 222 includes a fixing mechanism 229 for fixing the inserting unit 223 inside the heat transfer tube 5. The fixing mechanism 229 is provided at the detecting unit 224 or at a portion fixed to the detecting unit 224. The fixing mechanism 229 includes: an actuator 229a formed by a pneumatic cylinder, a hydraulic cylinder, an electric motor, a hydraulic motor, or the like; an actuating member 229b moved by the actuator 229a along the central axis C2; and movable members 229c provided movably along with the movement of the actuating member 229b in a radiation direction with a center thereof being the central axis C2 of the inserting unit 223. The actuating member 229b is formed in a wedge shape. The movable members 229c are provided in abutment with the wedge portion of the actuating member 229b. Therefore, according to the present embodiment, if the actuating member 229b is moved upward in FIG. 6 by the actuator 229a, the movable members 229c are moved outward in the radiation direction of the central axis C2. As a result, the contact member 223a is pressed against the inner peripheral surface of the heat transfer tube 5 via the bearings 223b, thereby fixing the inserting unit 223 inside the heat transfer tube 5. On the other hand, if the actuating member 229b is moved downward in FIG. 6 by the actuator 229a, the movable members 229c are moved inward in the radiation direction of the central axis C2. As a result, the contact member 223a is spaced apart from the inner peripheral surface of the heat transfer tube 5, thereby releasing the fixation of the inserting unit 223. Note that when the above-described fixing mechanism 229 is provided, the contact member 223a does not have to be elastically deformed.

Although the above-described inspecting probe unit 222 may have a single configuration, a plurality of sets of the inspecting probe unit 222 (in the present embodiment, two sets as shown in FIGS. 2, 4, and 5) may be provided with a distance between the central axes C2 being based on an arrangement distance between the heat transfer tubes 5. In this case, the inserting unit 223, the detecting unit 224, the rotating mechanism 225, the moving mechanism 226, the slide movement mechanism 227, the rotation angle detecting means 228, and the fixing mechanism 229 form one unit, and a plurality of such units are provided. Alternatively, the inserting unit 223, the detecting unit 224, the rotating mechanism 225, the slide movement mechanism 227, the rotation angle detecting means 228, and the fixing mechanism 229 may form one unit, a plurality of such units may be provided, and the moving mechanism 226 may move the all units together. In a case of the configuration in which the moving mechanism 226 moves all the units together, although not explicitly shown in the drawing, the slide movement mechanism is configured such that the inserting unit 223, the detecting unit 224, the rotating mechanism 225, the rotation angle detecting means 228, and the fixing mechanism 229 are disposed on the slide table as one set, and slides the slide table in each set. Moreover, in a case of the configuration in which the moving mechanism 226 moves all the units together, although not explicitly shown in the drawing, the slide movement mechanism is configured such that the inserting unit 223, the detecting unit 224, the rotating mechanism 225, the rotation angle detecting means 228, the fixing mechanism 229 and one moving mechanism are disposed on one slide table together, and slides this one slide table.

Figure 8:
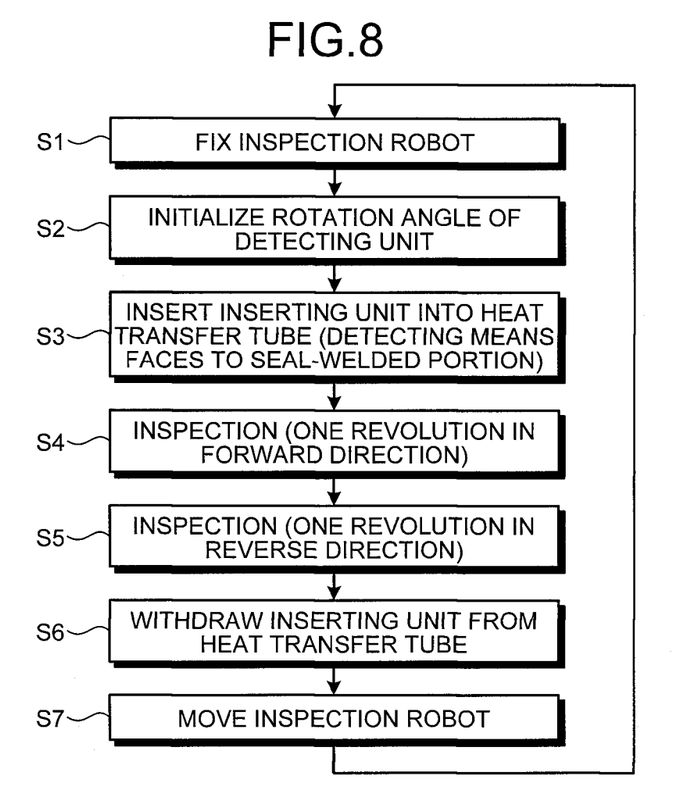
FIG. 8 is a flow chart showing a heat transfer tube inspection method according to an embodiment of the present invention.

An operation of the above-described inspection apparatus 20, and an inspection method using the above-described inspection apparatus 20 will be described below. FIG. 8 is a flow chart showing a heat transfer tube inspection method according to the present embodiment.

As shown in FIG. 8, first, the inspection robot 21 is fixed to the tube plate surface of the tube plate 4 so that the inspecting probe unit 222 is positioned directly below the heat transfer tube 5 to be inspected (step S1: see FIG. 4). That is, the central axis C1 of the heat transfer tube 5 to be inspected is caused to coincide with the central axis C2 of the inspecting probe unit 222. Here, the inserting unit 223 is at a position withdrawn from the heat transfer tube 5, thereby not inhibiting the movement of the inspection robot 21. Next, a rotational position of the detecting means 224c is detected by the rotation angle detecting means 228, and initialization thereof is performed with a predetermined rotation angle being 0 degrees (step S2). As a result, the rotational position of the detecting means 224c is aligned so as to correspond to the direction in which the heat transfer tube 5 to be inspected is attached to the tube plate 4. Next, the inserting unit 223 is moved (raised) along the central axis C2 by the moving mechanism 226, thereby inserting the inserting unit 223 into the heat transfer tube 5 to be inspected (step S3: see FIG. 5). As a result, the detecting means 224c faces to the seal-welded portion W of the heat transfer tube 5 to be inspected. Next, an inspection for the seal-welded portion W is performed (step S4). In the inspection of such a step S4, the detecting unit 224 is rotated by one revolution in one direction (forward direction) by the rotating mechanism 225 from the rotational position of the detecting means 224c initialized in step S2. Thus, the detecting means 224c is rotated by one revolution along the circumferential direction of the seal-welded portion W, and the presence or absence of a defect in the seal-welded portion W is thereby inspected. Next, an inspection of the seal-welded portion W is performed again (step S5). In the inspection of such a step S5, the detecting unit 224 is rotated by one revolution in the other direction (reverse direction) by the rotating mechanism 225 from the rotational position of the detecting means 224c initialized in step S2. Thus, the detecting means 224c is rotated by one revolution along the circumferential direction of the seal-welded portion W, and the presence or absence of a defect in the seal-welded portion W is thereby inspected. Next, the inserting unit 223 is moved (lowered) along the central axis C2 by the moving mechanism 226, thereby pulling out the inserting unit 223 from the inspected heat transfer tube 5 (step S6). Next, the inspection robot 21 is moved so that the inspecting probe unit 222 is positioned directly below the heat transfer tube 5 to be inspected next (step S7). By repeating the operations of steps S1 to S7, a plurality of heat transfer tubes 5 are inspected.

Note that in the operation (inspection method) of the above-described inspection apparatus 20, since steps S4 and S5 for inspecting the presence or absence of a defect in the seal-welded portion W can obtain inspection signals in both of the forward and reverse rotations, more accurate inspection can be performed. Note however that any one of steps S4 and S5 may be performed for inspecting the presence or absence of a defect in the seal-welded portion W.

As described above, the inspection apparatus 20 for the heat transfer tube 5 according to the present embodiment is provided in the inspection robot (fixed means) 21 to be fixed on the tube plate surface of the tube plate 4 at which the heat transfer tube 5 is opened, and is for inspecting the seal-welded portion W at which the heat transfer tube 5 is welded to the tube plate 4. The inspection apparatus 20 for the heat transfer tube 5 includes: the inserting unit 223 to be inserted into and withdrawn from the heat transfer tube 5; the detecting unit 224 having the detecting means 224c for detecting the presence or absence of a defect at the seal-welded portion W; the rotating mechanism 225 for rotating the detecting unit 224 around the central axis C2 of the inserting unit 223; and the moving mechanism 226 for moving, with respect to the inspection robot 21, the inserting unit 223, the detecting unit 224, and the rotating mechanism 225 along the central axis C2 for the rotation of the detecting unit 224.

According to this inspection apparatus 20 for the heat transfer tube 5, the moving mechanism 226 moves the inserting unit 223, the detecting unit 224, and the rotating mechanism 225 along the central axis C2 for the rotation of the detecting unit 224. As a result, while it becomes possible to insert the inserting unit 223 into the heat transfer tube 5 to be inspected and to detect the presence or absence of a defect in the seal-welded portion W of the heat transfer tube 5 by the detecting means 224c, it becomes possible to withdraw the inserting unit 223 from the heat transfer tube 5 and to move the inspection robot 21 to a position of another heat transfer tube 5 to be inspected. As a result, it becomes possible to inspect the seal-welded portion W of the heat transfer tube 5 by a remote control.

Moreover, the inspection apparatus 20 for the heat transfer tube 5 according to the present embodiment includes the slide movement mechanism 227 for sliding, with respect to the inspection robot 21, at least the inserting unit 223, the detecting unit 224, and the rotating mechanism 225 in a direction perpendicular to the central axis C2 for the rotation of the detecting unit 224.

According to this inspection apparatus 20 for the heat transfer tube 5, even if the position of the central axis C2 for the rotation of the detecting unit 224 is misaligned with respect to the heat transfer tube 5 to be inspected, by sliding the inserting unit 223, the detecting unit 224, and the rotating mechanism 225 by means of the slide movement mechanism 227 in a direction perpendicular to the central axis C2 for the rotation of the detecting unit 224, such misalignment is absorbed. Then, while the inserting unit 223 is inserted into the heat transfer tube 5 to be inspected, the detecting unit 224 is rotated along the seal-welded portion W of the heat transfer tube 5. Therefore, it becomes possible to improve the inspection accuracy thereof.

Moreover, the inspection apparatus 20 for the heat transfer tube 5 according to the present embodiment includes the rotation angle detecting means 228 for detecting a rotation angle of the detecting unit 224.

According to this inspection apparatus 20 for the heat transfer tube 5, the rotational position of the detecting means 224c can be aligned so as to correspond to the direction in which the heat transfer tube 5 is attached to the tube plate 4. As a result, it facilitates to identify the position at which a defect of the seal-welded portion W is detected, thereby improving the inspection accuracy.

Moreover, the inspection apparatus 20 for the heat transfer tube 5 according to the present embodiment includes the fixing mechanism 229 provided to the inserting unit 223 for fixing the inserting unit 223 inside the heat transfer tube 5.

According to this inspection apparatus 20 for the heat transfer tube 5, when the detecting unit 224 is rotated, positional misalignment in the central axis C2 for the rotation thereof is prevented from occurring, thereby rotating the detecting unit 224 along the seal-welded portion W of the heat transfer tube 5. Thus, it becomes possible to improve the inspection accuracy.

Moreover, the inspection apparatus 20 for the heat transfer tube 5 according to the present embodiment includes a plurality of sets of at least the inserting unit 223, the detecting unit 224, and the rotating mechanism 225 with a distance between the central axes C2 being based on an arrangement distance between the heat transfer tubes 5.

According to this inspection apparatus 20 for the heat transfer tube 5, a plurality of heat transfer tubes 5 to be inspected can be simultaneously inspected, thereby making it possible to shorten the inspection time.

Moreover, in a case where the inspection apparatus 20 for the heat transfer tube 5 according to the present embodiment includes a plurality of sets of at least the inserting unit 223, the detecting unit 224, and the rotating mechanism 225 with a distance between the central axes C2 being based on an arrangement distance between the heat transfer tubes 5, the inspection apparatus 20 includes the moving mechanism 226 for each set.

For example, in the steam generator 1, in a case where a stay rod provided between the respective tube support plates 6 for supporting the heat transfer tubes 5 is disposed between the heat transfer tubes 5, or in a case where the heat transfer tube 5 is disposed at a peripheral portion of the tube plate 4 although not explicitly shown in the drawing, there is a case where all of the sets cannot be used. Therefore, according to this inspection apparatus 20 for the heat transfer tube 5, the inserting unit 223, the detecting unit 224, and the rotating mechanism 225 disposed at a portion where no heat transfer tube 5 is positioned are not moved, whereas the inserting unit 223, the detecting unit 224, and the rotating mechanism 225 disposed at a portion where the heat transfer tube 5 is positioned are moved by the moving mechanism 226. Thus, it becomes possible to perform inspection without blind spots.

Moreover, the inspection method for the heat transfer tube 5 according to the present embodiment is an inspection method for the heat transfer tube 5, which inspects the seal-welded portion W at which the heat transfer tube 5 is welded to the tube plate 4 by using the inspection apparatus 20 which is provided in the inspection robot (fixed means) 21 to be fixed on the tube plate surface of the tube plate 4 where the heat transfer tube 5 is opened and which includes: the inserting unit 223 to be inserted into and withdrawn from the heat transfer tube 5; the detecting unit 224 having the detecting means 224c for detecting the presence or absence of a defect at the seal-welded portion W; the rotating mechanism 225 for rotating the detecting unit 224 around the central axis C2 of the inserting unit 223; the moving mechanism 226 for moving, with respect to the inspection robot 21, the inserting unit 223, the detecting unit 224, and the rotating mechanism 225 along the central axis C2 for the rotation of the detecting unit 224; and the rotation angle detecting means 228 for detecting a rotation angle of the detecting unit 224. The inspection method for the heat transfer tube 5 according to the present embodiment includes: a step of detecting a rotation angle of the detecting unit 224 by the rotation angle detecting means 228 with the inspection robot 21 being fixed to the tube plate surface of the tube plate 4; a next step of moving the inserting unit 223 by the moving mechanism 226 to insert the inserting unit 223 into the heat transfer tube 5 and to cause the detecting means 224c of the detecting unit 224 to face to the seal-welded portion W; and a next step of rotating the detecting unit 224 by the rotating mechanism 225 based on the detected rotation angle.

According to this inspection method for the heat transfer tube 5, the moving mechanism 226 moves the inserting unit 223, the detecting unit 224, and the rotating mechanism 225 along the central axis C2 for the rotation of the detecting unit 224. As a result, while it becomes possible to insert the inserting unit 223 into the heat transfer tube 5 to be inspected and to detect the presence or absence of a defect in the seal-welded portion W of the heat transfer tube 5 by the detecting means 224c, it becomes possible to withdraw the inserting unit 223 from the heat transfer tube 5 and to move the inspection robot 21 to a position of another heat transfer tube 5 to be inspected. As a result, it becomes possible to inspect the seal-welded portion W of the heat transfer tube 5 by a remote control. Furthermore, with the step of detecting a rotation angle of the detecting unit 224 by the rotation angle detecting means 228, the rotational position of the detecting means 224c can be aligned so as to correspond to the direction in which the heat transfer tube 5 is attached to the tube plate 4. As a result, it facilitates to identify the position at which a defect of the seal-welded portion W is detected, thereby improving the inspection accuracy.

Moreover, according to the inspection method for the heat transfer tube 5 in the present embodiment, the detecting unit 224 is rotated in the forward and reverse directions around the central axis C2 in the step of rotating the detecting unit 224 by the rotating mechanism 225.

According to this inspection method for the heat transfer tube 5, by rotating the detecting unit 224 in the forward and reverse directions around the central axis C2, it is possible to make a determination based on the combination of the inspection signals in both of the forward and reverse rotations. Therefore, more accurate inspection can be performed.

REFERENCE SIGNS LIST 1 steam generator
4 tube plate
5 heat transfer tube
7 water chamber
7C manhole
20 inspection apparatus
21 inspection robot
22 inspection unit
221 attachment base
222 inspecting probe unit
223 inserting unit
223a contact member
223b bearing
224 detecting unit
224a columnar portion
224b flange portion
224c detecting means
224ca contact
224cb ECT coil
224cc pressing portion
225 rotating mechanism
226 moving mechanism
226a support base
226b roller
226c belt
226d motor
227 slide movement mechanism
227a slide table
227b slide rail
227c slider
227d slide rail
227e slider
228 rotation angle detecting means
229 fixing mechanism
229a actuator
229b actuating member
229c movable member
C1 central axis
C2 central axis
W seal-welded portion

The invention claimed is:

1. A heat transfer tube inspection apparatus provided in a fixed unit to be fixed to a tube plate surface of a tube plate at which a heat transfer tube is opened, for inspecting a seal-welded portion at which the heat transfer tube is welded to the tube plate, the inspection apparatus comprising:
an inserting unit to be inserted into and withdrawn from the heat transfer tube;
a detecting unit for detecting a presence or absence of a defect at the seal-welded portion;
a rotating mechanism for rotating the detecting unit around a central axis of the inserting unit; and
a moving mechanism for moving, with respect to the fixed unit, the inserting unit, the detecting unit, and the rotating mechanism along the central axis for the rotation of the detecting unit; wherein
the inserting unit includes a fixing mechanism that fixes the inserting unit inside the heat transfer tube and a contact member that is pressed against an inner surface of the transfer tube,
the fixing mechanism includes an actuator and a movable member that is disposed inside the contact member and is moved in a direction perpendicular to the central axis by the actuator,
the inserting unit further includes a bearing between the contact member and the movable member to allow the contact member and the movable member to mutually rotate about the central axis.

2. The heat transfer tube inspection apparatus according to claim 1, further comprising a slide movement mechanism for sliding, with respect to the fixed unit, at least the inserting unit, the detecting unit, and the rotating mechanism in the direction perpendicular to the central axis for the rotation of the detecting unit.

3. The heat transfer tube inspection apparatus according to claim 1, further comprising a rotation angle detecting unit for detecting a rotation angle of the detecting unit.

4. The heat transfer tube inspection apparatus according to claim 1, wherein a plurality of sets of at least the inserting unit, the detecting unit, and the rotating mechanism are provided with a distance between the central axes thereof being based on an arrangement distance between the heat transfer tubes.

5. The heat transfer tube inspection apparatus according to claim 4, wherein the moving mechanism is provided for each of the sets.

6. A heat transfer tube inspection method for inspecting a seal-welded portion at which a heat transfer tube is welded to a tube plate by using the inspection apparatus according to claim 1, the inspection method comprising:
detecting a rotation angle of the detecting unit by a rotation angle detecting unit with the fixed unit being fixed to the tube plate surface of the tube plate;
next, moving the inserting unit by the moving mechanism to insert the inserting unit into the heat transfer tube and to cause the detecting unit to face to the seal-welded portion; and
next, rotating the detecting unit by the rotating mechanism based on the detected rotation angle.

7. The heat transfer tube inspection method according to claim 6, wherein the detecting unit is rotated in forward and reverse directions around the central axis in the rotating the detecting unit by the rotating mechanism.

* * * * *